(12) United States Patent
Teufelberger et al.

(10) Patent No.: US 7,972,135 B2
(45) Date of Patent: Jul. 5, 2011

(54) DENTAL HANDPIECE FOR ROOT CANAL TREATMENT AND METHOD

(75) Inventors: Gunter Teufelberger, Bürmoos (AT); Andreas Brandstaetter, St. Pantaleon (AT); Nikolaus Pfaffinger, St. Pantaleon (AT); Josef Spitzauer, Oberndorf (AT)

(73) Assignee: W&H Dentalwerk Bürmoos GmbH, Bürmoos (AT)

( * ) Notice: Subject to any disclaimer, the term of this patent is extended or adjusted under 35 U.S.C. 154(b) by 343 days.

(21) Appl. No.: 12/239,608

(22) Filed: Sep. 26, 2008

(65) Prior Publication Data

US 2009/0087814 A1     Apr. 2, 2009

(30) Foreign Application Priority Data

Sep. 27, 2007   (EP) ..................... 07018998

(51) Int. Cl.
*A61C 1/08*   (2006.01)
*A61C 19/04*  (2006.01)
(52) U.S. Cl. .......................... 433/72; 433/75
(58) Field of Classification Search ............... 433/27, 433/72, 75, 77, 102, 126, 131
See application file for complete search history.

(56) References Cited

U.S. PATENT DOCUMENTS

| | | | | |
|---|---|---|---|---|
| 4,243,388 A * | 1/1981 | Arai | ................................ | 433/27 |
| 4,486,176 A * | 12/1984 | Tardieu et al. | ................ | 433/133 |
| 5,897,315 A * | 4/1999 | Nakayama et al. | ............. | 433/72 |
| 5,902,105 A * | 5/1999 | Uejima et al. | .................. | 433/27 |
| 7,070,411 B2 * | 7/2006 | Nakanishi et al. | .............. | 433/72 |
| 7,452,208 B2 * | 11/2008 | Eibl et al. | ......................... | 433/72 |
| 7,476,101 B2 * | 1/2009 | McPherson et al. | ............. | 433/75 |
| 7,628,613 B2 * | 12/2009 | Becker et al. | ................. | 433/126 |
| 7,758,342 B2 * | 7/2010 | Lewallen et al. | ................ | 433/27 |
| 7,771,197 B2 * | 8/2010 | Eibl et al. | ......................... | 433/72 |
| 2007/0065774 A1 * | 3/2007 | Pernot et al. | .................. | 433/126 |

FOREIGN PATENT DOCUMENTS

| | | |
|---|---|---|
| DE | 195 20765 | 12/1995 |
| EP | 1 642 547 | 4/2006 |
| FR | 2 864 442 | 7/2005 |

OTHER PUBLICATIONS

European Search Report for EP 07 01 8998 (mailed Feb. 20, 2008).

\* cited by examiner

*Primary Examiner* — Ralph A Lewis
(74) *Attorney, Agent, or Firm* — Klarquist Sparkman, LLP

(57) ABSTRACT

A dental handpiece for root canal treatment comprises an outer sleeve, a connecting device for connecting the handpiece to a control and analyzing unit, a measurement circuit having a power source and to a drive unit, an electrically conducting tool receptacle and an electrically conducting driving device, wherein the tool receptacle and the driving device are mechanically and electrically connected together so that a driving motion generated by the drive unit can be transmitted via the driving device to the tool receptacle and electrical measurement signals can be transmitted between the driving device and the tool receptacle. A first connection is provided for transmitting the driving motion. A second electrically conducting connection, which may comprise sliding contacts, is provided for transmitting the electrical measurement signals. With separate connections, an improved signal transmission and in particular a low loss of measurement signals of the root canal length measurement during the signal transmission are achieved.

20 Claims, 2 Drawing Sheets

DENTAL HANDPIECE FOR ROOT CANAL TREATMENT AND METHOD

CROSS REFERENCE TO RELATED APPLICATION

The present application claims priority from pending European Patent Application No. 07018998.0 filed Sep. 27, 2007, which is incorporated herein by reference.

BACKGROUND

1. Field

The present invention relates to a dental handpiece for root canal treatment and in particular for measuring the length of a root canal.

2. Description of Prior Art

Such a handpiece is known from European Patent Application EP 1,642,547 A1 (the '547 application), which is incorporated herein by reference. The handpiece disclosed in the '547 application has a device for transmitting electrical measurement signals of the root canal length measurement, which is formed by the elements for transmitting the driving motion, in particular by the drive shafts, the gears and gearwheels of the handpiece.

Transmission of the electrical measurement signals of the root canal length measurement by the mechanical transmission elements has the advantage that existing components can be used for conducting the measurement signal. However, it is a disadvantage that the quality of the signal transmission is sometimes low and in particular that some measurement signals are lost, especially in the area of the interfaces between the elements for transmission of the driving motion, e.g., between individual shafts or shaft parts.

There is thus an advantage in a handpiece for root canal treatment with a device for transmission of the measurement signals which is formed by the elements for transmitting the driving motion such that an improved secure signal transmission and in particular a reduced loss of measurement signals during the signal transmission is ensured. In addition, a method for manufacturing a handpiece with an improved signal transmission would also be advantageous.

Another disadvantage of the handpiece described in the '547 application is that further conduction of the measurement signals takes place at the connection end of the handpiece via the driving element to a shaft of a connecting part, e.g., a coupling, connected thereto. There is thus another interface between shafts that are detachably connected to one another and subject to some play, resulting in inadequate signal transmission and loss of measurement signals. In addition, conducting the measurement signals further via the dog shaft portion of the handpiece requires a suitably complex design of the connecting part with electrical insulation of the shaft of the connecting part.

Thus, it would be advantageous to provide a handpiece for root canal treatment which will allow an improved conduction of the measurement signals to the connecting part.

SUMMARY

According to one embodiment, the dental handpiece for root canal treatment and in particular for measurement of the length of a root canal comprises an outer sleeve, a connecting device for connecting the handpiece to a control and analyzing unit, to a measurement circuit with a power source and to a drive unit, an electrically conducting tool receptacle and an electrically conducting driving device. The driving device can be mechanically connected, i.e., drivingly coupled, to the tool receptacle so that a driving motion generated by the drive unit can be transmitted from the driving device to the tool receptacle. Further, the tool receptacle and the driving device can be electrically linked or connected such that electrical measurement signals can be transmitted between the driving device and the tool receptacle. A first connection is provided for transmitting the driving motion from the driving device to the tool receptacle. A second connection is capable of transmitting electrical measurement signals between the driving device and the tool receptacle. In some embodiments, the second connection comprises at least one sliding contact.

This embodiment has the advantage that due to the separation of the electrical and mechanical connecting functions into separate connections, i.e., the mechanical first connection and the electrical second connection, transmission of the electrical measurement signals does not take place or at least not exclusively via the first connection for driving motion, as is known from the state of the art. The components of the first connection for driving motion, which include gearwheels, pinions, eccentric pins and other gear parts, for example, come in contact with one another with certain amounts of play, so these components intermittently separate during the operation of the handpiece, and thus conduction of electrical signals can be interrupted. A high measurement frequency is used during the determination of the root canal depth, and up to 2,000 measurement signals per second are generated. In addition, such treatments requiring root canal length measurement are extremely delicate and demanding, so interruptions in signal conduction, which are associated with a loss of measurement signals and measurement data, are not acceptable. These disadvantages are addressed by the embodiments of this application.

The design of the second connection as a sliding contact in some embodiments guarantees an especially reliable signal transmission, regardless of the rotational speeds of the tool receptacle and the driving device, which are variable and may even be different. The sliding contacts are designed in particular so that they compensate for or bridge the play and separation between the transmission components of the first connection for driving motion, so that there is a continuous electrical connection between the tool receptacle and the driving device and there is no interruption in the signal conduction. This is achieved in one embodiment by providing a second connection that is movable, in particular displaceable, with respect to the first connection, so that a relative movement between the tool receptacle and the drive unit can be compensated. Alternatively, the second connection can have a variable length extent.

In a preferred embodiment, the second connection is therefore designed to be elastic or resilient and, especially preferably, to include a spring element, such as a spiral spring. Depending on the embodiment, the spring element prestresses additional components of the second connection against the tool receptacle and/or the driving device to ensure signal conduction therethrough, or itself conducts the measurement signals directly or indirectly. In an especially preferred embodiment, the spring element or the ends thereof directly contact the tool receptacle and the driving device and conducts the measurement signals between them, so that an extremely simple and inexpensive design of the second connecting means is implementable.

In one embodiment, the outer sleeve is constructed in several parts. In particular the handpiece head and the handle-and-neck part connected thereto can be separated from one another. In a preferred embodiment, the outer sleeve is designed in one piece, so that it also comprises the handpiece head, which greatly facilitates assembly of the handpiece.

The connecting device of the handpiece is preferably designed as a known plug or plug-and-turn coupling which has connections to a control and analyzer unit, a measurement circuit with a power source and to a drive unit. In a preferred embodiment, the drive unit, which is designed as an electrical motor, a compressed gas-operated motor or a vibrating drive, is coupled directly to the handpiece and/or to the connecting device. The control and analyzing unit as well as the measurement circuit with the power source are contained in the handpiece either completely or partially, or are completely or partially contained in a separate control unit, which is or can be connected to the handpiece in a known way via a supply tube.

The electrically conducting tool receptacle is designed as a frictional or a positive metallic tool receptacle for detachable connection of a tool, e.g., a rotary drill, a file that can move back and forth or a reamer. It is accommodated and supported in the handpiece head in a known way such that a rotating movement or a lifting movement can be induced by the driving device.

The driving device extends from the connecting device through the handle part and neck part of the handpiece up to the tool receptacle and transmits the driving motion generated by the drive unit to the tool receptacle. In one embodiment, the driving device comprises several shafts or shaft parts, which are arranged at least partially at an angle to one another and may be connected to one another by one or more gears. In a preferred embodiment which is described in greater detail below, the driving device is designed to be essentially straight. At least one part of the driving device, e.g., a shaft or a shaft section, is made of an electrically conducting material, in particular steel, so that it serves to transmit the electrical measurement signals of the root channel length measurement and thus is part of a device for transmitting electrical measurement signals (i.e., part of a signal transmitting circuit or assembly).

The tool receptacle is driven via the first mechanical connection for driving motion, e.g., using gearwheels, pinions, eccentric pins or elongated holes for cams. On the basis of the second electrical connection for transmitting the electrical measurement signals, it is not necessary for the components of the first connection to be made of electrically conducting materials. In one embodiment, these components are made of or are coated with an electrical insulation material, e.g., a ceramic, so they serve as electrical insulators, e.g., to insulate the metallic outer sleeve of the handpiece. In another embodiment, the first connection comprises one or more electrically conducting materials (e.g., a metal, in particular steel) so that the components of the first connection transmit electrical measurement signals of the root canal length measurement in addition to the second connection's role in securely transmitting the signal transmission. In this way, redundant signal transmission capability can be provided.

In another embodiment, the components of the second connection are mounted on the driving device and are pre-stressed into contact against the tool receptacle, with the second connection components preferably arranged at least partially in a receptacle of the driving device. Because of the small amount of space available in handpieces, in particular in the handpiece head, and in the area of the transition from the handpiece head to the neck part, this embodiment of the handpiece is of great benefit because the second connection arranged in and/or on the driving device and/or in the drive shaft take up little additional space.

In one embodiment, the first and second connections contact the tool receptacle at different locations. This spatial separation of the contact points on the tool receptacle has the advantage that lubricant or friction-reducing additives or coatings, which are necessary in particular for permanent and low-wear functioning of the first connection components, but which can influence or suppress the transmission of the electrical measurement signals, may be applied and used at a distance from the second connection.

In another embodiment, the second connection can have a pin or a sleeve with a rounded end, in particular a spherical end. Therefore in an advantageous manner, the contact face between the tool receptacle and the second connection and thus the frictional resistance, the abrasion and additional noise emissions, are minimized. As an alternative, the sliding contacts can be brushes made of graphite and/or metal.

In another embodiment, the handpiece has a handle part, a neck part arranged at an angle to the handle part and a handpiece head arranged at an angle to the neck part, with the tool receptacle being arranged in the handpiece head and the driving device comprising an essentially straight driveshaft which passes through the handle part and the neck part. The drive shaft in particular comprises several shaft parts, which are joined together in a twist-proof manner. This embodiment of the handpiece has the advantage that no gearing or other loosely connected coupling elements for connecting shafts or shaft parts are required, which reduces interruptions or influence in the electrical measurement signal transmission over the entire length of the driveshaft. This advantage is manifested especially with a shaft designed in one piece, but it also exists with multipart driveshafts with which the shaft parts are connected together securely, are difficult to separate from one another or cannot be separated at all or are connected together in an essentially twist-proof manner, e.g., by a positive or frictional connection, by pressing or by welding. This embodiment of the handpiece advantageously contributes toward an improved and more reliable signal transmission and toward a reduced loss of measurement signals.

Due to the straight, one-piece or multi-piece design of the driveshaft described above, in a preferred embodiment, it is possible to support the driveshaft with only two bearings, in particular with two roller bearings or ball bearings. This reduces the noise generated during operation of the handpiece in an advantageous manner, while also reducing its manufacturing costs.

According to another embodiment, at least one part of the overall system or assembly with which electrical measurement signals are transmitted is provided with a coating for conducting the electrical measurement signals, with the electrical conductivity of the coating being greater than the electrical conductivity of steel. The coating can comprise, for example, at least one of copper, silver and gold. This covering or lining of at least some parts of the system for transmitting electrical measurement signals, e.g., of the tool receptacle, of one or more drive shafts or shaft parts, of the connecting device, of the second connecting connection between the tool receptacle and the driving device or of other components has surprisingly yielded a great quality improvement in the measurement signal transmission in experiments. This was achieved in particular when all the components of the system for transmitting electrical measurement signals were coated.

In one embodiment, the coating is designed in multiple layers, at least one layer being designed as an adhesive layer and being arranged between the surface of the coated component and one or more other layers. Because of the many components of the device for transmission of electrical measurement signals, where the components move in relation to one another and come in contact with one another, such a design is of great advantage in preventing abrasion and maintaining intactness and the most complete possible functionality of the coating. The coating can comprise at least one adhesive layer that has the same or similar composition as one of the other layers of the coating, in one embodiment. In another embodiment, the adhesive layer comprises nickel. In an especially preferred embodiment, the coating comprises a nickel layer, an adhesive gold layer and a pure gold layer. All three layers are preferably applied to the outer sleeve of the handpiece by electroplating and have layer thicknesses of approximately 0.2 μm to approximately 2.5 μm.

In one embodiment, at least one part of the assembly for transmitting electrical measurement signals, which is provided with a coating for conducting the electrical measurement signals, is smoothed at the surface, in particular by electrolytic polishing. This yields an improved adhesion of the coating to the device for transmission of electrical measurement signals.

According to one embodiment, the assembly for transmitting electrical measurement signals comprises at least one electrically conducting wire, which is electrically connected to the driving device and which serves to conduct the electrical measurement signals from the driving device. As a result of this measure, an improved, reliable and simplified further conduction of the measurement signals to the connecting device, e.g., a coupling, or to a drive unit with a motor, is made possible in an advantageous manner. In addition, this eliminates the need for furnishing the connecting device with electrical insulation of the shaft in the connecting device. In a preferred embodiment, conduction takes place via a plug contact to an electrically insulated wire or cable arranged in the connecting device.

The wire/several wires for relaying the measurement signals is/are preferably surrounded by electrical insulation and in particular are combined with an insulating outer sheath to form a cable so that interference with other components from the transmission of the measurement signals through the cable is suppressed.

In one embodiment, a third connection, which is designed to be elastic or resilient, is provided for connecting the wire to the driving device. In this embodiment, reliable electrical contact between the wire and the driving device is created, so that relative movements between the wire and the driving device, in particular vibration of the driving device, can be compensated. The third connecting connection preferably comprises a spring element, in particular a spiral spring.

In another embodiment, the third connection comprises a pin or a sleeve with a rounded end, in particular a spherical end. Therefore, in an advantageous manner, the contact face between the driving device and the third connection, and thus the frictional resistance, the abrasion and additional noise emissions are minimized. The third connection may of course also have other contact elements or components, e.g., graphite brushes and/or metal brushes.

In one embodiment, the third connection includes one or more components that protrude through a bearing sleeve of the driving device and/or are attached therein. This allows in an advantageous manner an extremely space-saving installation of the third connection and of the fastening elements for securing the third connection components in the handpiece. The fastening elements may comprise, for example, a thread.

In one embodiment, one or more electrical insulating portions (or insulators) can be arranged on the driving device, which is part of the assembly for transmitting the electrical measurement signals, the electrical insulation providing insulation for a connectable part or component to reduce interference that could arise from the transmission of electrical measurement signals. The connectable part or component is defined herein to comprise a component that can be or is connected to the connecting device. One example of a connectable component is a motor. The electrical insulation ensures that the component (e.g., the motor), and its elements (such as electrical or electronic elements, which include circuits, sensors, etc.), are reliably electrically insulated from the assembly that conducts the electrical measurement signals when connected to the drive unit of the handpiece.

In one embodiment, an insulator is arranged in the handpiece, on the driving device or as part of the driving device. This has the advantage that each connectable component connected to the handpiece, regardless of its design and regardless of whether the component itself has electrical insulation, is insulated electrically from the driving device and thus is insulated from the transmission of electrical measurement signals). The insulator can include, for example, a shaft or a shaft part, a journal or a sleeve made of ceramic or plastic. In another embodiment, the insulator is formed on the connectable component or as a part thereof and can be arranged on the handpiece when the connectable component is coupled to the handpiece.

In one embodiment, the handpiece comprises an outer sleeve made of an electrically non-insulating material, preferably metallic, and there is an insulating portion for electrically insulating the system for transmission of electrical measurement signals from the outer sleeve. This creates a handpiece that is simple to manufacture and is not sensitive to cleaning processes, in particular to steam sterilization. Roller bearings with non-conducting components, in particular ceramic components, plastic sheathing for wires and cables and handpiece components, e.g., bushings, retaining rings, etc., that are made of or coated with plastic or ceramic, can be used as this insulator, which is sometimes referred to herein as a second insulator or second insulating portion.

A method for manufacturing a handpiece having improved signal transmission comprises:
  providing a dental handpiece for root canal treatment, having an outer sleeve,
  providing a connecting device for connecting the handpiece to a control and analyzing unit, to a measurement circuit with a power source and to a drive unit, an electrically conducting tool receptacle, an electrically conducting driving device,
  drivingly coupling the driving device to the tool receptacle, and
  electrically connecting the driving device and the tool receptacle for transmitting electrical measurement signals between the driving device and the tool receptacle.

In one embodiment, electrically connecting the driving device and the tool receptacle comprises connecting the driving device and the tool receptacle with at least one sliding contact.

In another process step, it is preferably provided that at least part in an overall assembly for transmitting electrical measurement signals, including at least one part of the tool receptacle and the driving device, for example, is provided with a coating for conducting the electrical measurement signals, the electrical conductivity thereof being higher than that of steel. The coating can comprise, for example, at least one of gold, silver and copper.

In another preferred embodiment, an additional process step comprises inserting at least one electrically conducting wire for conducting the electrical measurement signals away from the driving device into the handpiece, and electrically connecting the wire to the driving device.

These and other embodiments are explained in greater detail below on the basis of preferred embodiments and with reference to the accompanying drawings, in which:

DETAILED DESCRIPTION

Figure 1:
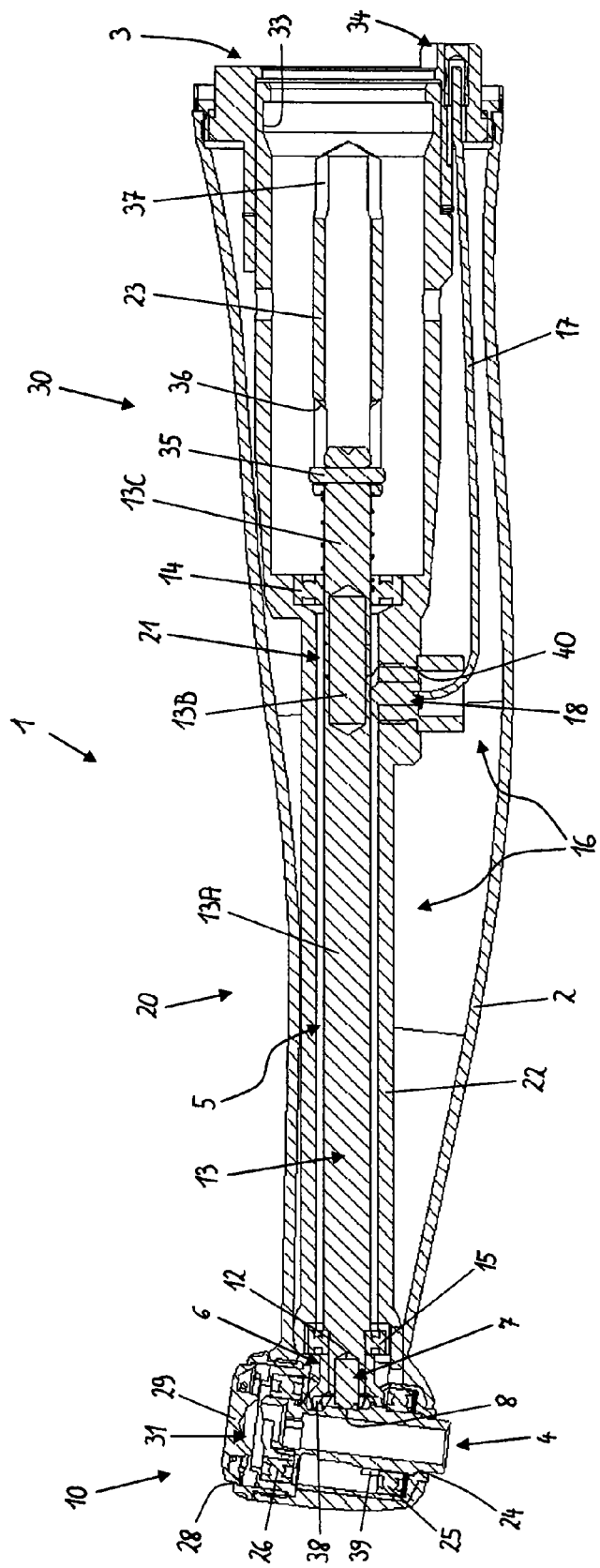
FIG. 1 is a longitudinal section view showing a dental handpiece for root canal treatment and in particular for measuring the length of a root canal.

The handpiece 1 for root canal treatment and in particular for measuring the length of a root canal, which is shown in FIG. 1 and is designed as a contra-angle handpiece, comprises a handpiece head 10, which is arranged at an angle greater than 90°, preferably approximately 92°-95°, to a neck part 20, and a handle part 30, which is connected to the neck part 20 at an angle of approximately 8°-16°. An outer sleeve 2 surrounds the handpiece 1, wherein the outer sleeve 2 including the handpiece head 10 is preferably designed in one piece.

Two openings opposite one another are provided on the handpiece head 10. The opening 24 serves as a tool receptacle opening through which a tool, e.g., a file or a drill, is detachably insertable into a tool receptacle 4 accommodated in the handpiece head 10. The tool receptacle 4 is mounted movably, in particular movably back and forth or rotatably in bearings 25, 26, as shown in FIG. 1.

Figure 2:
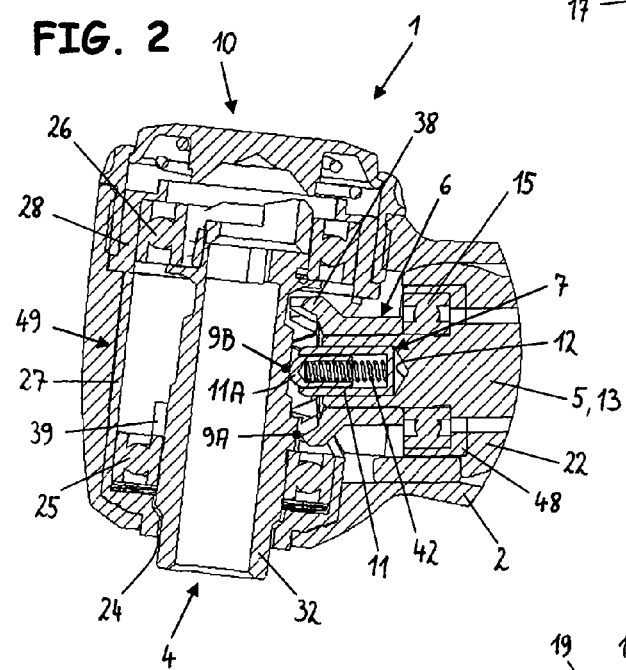
FIG. 2 is an enlarged view of the handpiece head of the handpiece according to FIG. 1.

The ball bearings 25, 26 and the tool receptacle 4 are accommodated in the handpiece head 10 in a sleeve or cartridge 49 which is formed by a bearing bushing 27 and a retaining ring 28, for example (see FIG. 2). The bearing bushing 27 and the retaining ring 28 may be designed in one piece or as separate components. They separate and insulate the ball bearings 25, 26 and the tool receptacle 4 completely from the outer sleeve 2 of the handpiece 1. The cartridge 49 is attached to shoulders and protrusions on the inside of the handpiece head sleeve and is secured by a threaded ring which is preferably part of a release mechanism 31 for releasing the tool. The cartridge 49 also has an opening through which a driving device 5 and the part of an assembly 16 that functions as a circuit to transmit the electrical measurement signals are connected to tool receptacle 4.

In the second opening 28 of the handpiece head 10, a displaceable pushbutton 29 is provided, which is part of a release mechanism 31 for the tool chucked in the tool receptacle 4. The design of the release mechanism 31 and the design of tool receptacle 4 are known, so they need not be described in detail here. Various embodiments may be used as the tool receptacle, e.g., force-fitting or form-fitting tool receptacles or combinations thereof. The tool receptacles preferably have a hollow shaft 32 into which the tool or a tool shaft can be inserted through an opening in the tool receptacle. A collet chuck or a form-fitting element, e.g., a thread may be provided on the hollow shaft 32 for securing the tool and/or for transmitting the torque.

On the end of handpiece 1 opposite the handpiece head 10 there is a connecting device 3 for connection of the handpiece 1 to a control and analyzing unit, to a measurement circuit with a power source and to a drive unit. The connecting device 3 is part of a coupling device, in particular a plug coupling or twist coupling for connecting the handpiece 1 to a connecting part, e.g., a drive unit having an electrical motor. It includes a coupling tube 33 into which a coupling journal of the connecting part can be inserted. A part of the driving device 5, e.g., hollow shaft 23 with dog 37 protrudes into the coupling tube 33 for connection to a shaft of the connecting part which is connected to the motor of the drive unit. The connecting device 3 also comprises a contact device 34, in particular a plug contact for transmitting the measurement signals of the root canal length measurement to the connecting part.

A driving device 5 for transmitting the driving motion to the tool receptacle 4 extends from the connecting device 3 to the tool receptacle 4 and/or between the connecting device 3 and the tool receptacle 4 through the handle part 3 and the neck part 20 of the handpiece 1. The driving device 5 is designed as a straight driveshaft 13, wherein it is arranged in the handpiece 1 in such a way that its ends are arranged approximately centrally in the outer sleeve 2 and/or in the handle part 30 and in the neck part 20, whereas a section between the two ends is situated eccentrically in the outer sleeve 2 and/or in the handle part 30 and/or in the neck part 20.

The driving motion and the torque are transmitted from the driving device 5 to the tool receptacle 4 via the first connection 6, which can comprise, e.g., two intermeshing gearwheels 38, 39. The first gearwheel 38 is mounted on the driving device 5, in particular being pressed on the driveshaft 13. The second gearwheel 39 is connected to the tool receptacle 4, in particular the hollow shaft 32, e.g., by pressing.

The driveshaft 13 comprises several shaft parts 13A, 13B, 13C as well as the hollow shaft 23, at least some of these shaft parts being pressed together, screwed together or otherwise connected together so that they essentially do not execute any rotational movement relative to one another. The shaft part 13C is connected to the hollow shaft 23 in a known manner by accommodating an end section of the shaft part 13C in the hollow shaft 23 and by a pin 35 which is attached transversely in the shaft part 13C, its ends protruding through slots 36 in the hollow shaft 23. The hollow shaft 23 is prestressed by a spring against the shaft part 13C, so that it is displaceable over the shaft part 13C.

Two roller bearings, in particular ball bearings 14, 15, support the drive shaft 13 in the handpiece 1. A bearing sleeve 22 surrounds the drive shaft 13 and serves as a bearing seat for the ball bearings 14, 15. At least the ball bearing 15, which is arranged closer to the handpiece head 10 is accommodated in a bearing element 48, e.g., a bearing cap which surrounds the ball bearing 15 in such a way that it does not have any direct contact with the bearing sleeve 22. The bearing sleeve 22 preferably extends up to the connecting device 3, wherein it has two sections with different inside diameters and wherein the section with the larger inside diameter forms the coupling tube 33.

Measurement signals or measurement data are sent from the tool which is accommodated in the tool receptacle 4 and serves as a measurement electrode, through the handpiece 1 to the connecting device 3 by the assembly 16 for transmitting the electrical measurement signals of the root canal length measurement. The assembly 16 for transmitting the electrical measurement signals, which functions as a circuit, is formed at least from parts or sections of the tool receptacle 4, the driving device 5 and a wire or cable 17, which protrudes from the connecting device 3 into the handle part 30 or the neck part 20. All these components are made of electrically conducting materials, in particular metals such as steel or copper.

To improve the transmission quality of the measurement signals, a second connection 7 for transmitting the electrical measurement signals is provided between the tool receptacle 4 and the driving device 5. As also seen in particular in FIG. 2, the second connection 7 is accommodated at least partially in a receptacle 12, which is preferably in the form of a blind hole bore. The second connection 7 preferably comprises a sliding contact 8.

The design of separate connections 6, 7 for mechanical coupling and electrical contacting has the advantage that transmission of the electrical measurement signals does not take place via the first connection 6 with the gearwheels 38, 39, or at least not exclusively, where there are repeated interruptions in signal transmission when the two gearwheels 38, 39 are uncoupled and disengaged. The gearwheels 38, 39 in some embodiments are also made of electrically conducting materials, however, so in these cases data transmission can also take place by way of the gearwheels 38, 39, which provides for certain benefits, including redundancy.

In the neck part 20 or in the handle part 30 is provided a third electrically conducting connection 18, by which the measurement signals are conducted from the driving device 5 to the wire 17. The third connection 18 is also designed as a sliding contact and protrudes through a borehole 40 in the bearing sleeve 22 to the driving device 5.

As already described, the driving device 5 comprises multiple shafts 13A, 13B 13C, 23, which are arranged in the neck part 20 or handle part 30 and which are connected directly or indirectly to the drive unit, in particular a motor, preferably an electrical motor. As also already explained above, parts of the driving device 5 are included in the assembly 16 for transmission of electrical measurement signals. To suppress the forwarding of the electrical measurement signals to the motor and to components connected thereto, a first insulator or electrically insulating portion 21 is therefore provided on the handpiece 1. The insulator 21, which is made of plastic or ceramic, for example, comprises the shaft part 13B and a bushing 41 surrounding the shaft part 13B (see FIG. 4). The shaft part 13B is inserted into a receptacle in each of the shaft parts 13A and 13C and pressed or glued therein. The bushing 41 is pushed onto the shaft part 13B and arranged between the two shaft parts 13A, 13C. The bushing 41 and the shaft part 13B may of course also be designed in one piece.

For the purpose of an improved measurement signal conduction of the root canal length measurement, at least one of the following components is provided with a surface coating which comprises at least one of gold, silver and copper. In a specific embodiment, the surface coating comprises gold, silver or copper in an amount of at least 50% on the tool receptacle 4, the second connection 7, the driving device 5 (in particular the shaft part 13A), the third connection 18, or at least one part of the contact device 34 (in particular the socket 45 (see FIG. 3)).

FIG. 2 shows an enlarged diagram of the handpiece head 10 of the handpiece 1 from FIG. 1, showing the detailed design of the second connection 7, designed as the sliding contact 8. An outer sleeve 11 is attached, e.g., by clamping, soldering and/or gluing, in the receptacle 12 of the driveshaft 13. A sliding sleeve with a rounded hemispherical end 11A which faces and comes in contact with the tool receptacle 4 is also situated in an opening of the outer sleeve 11 facing the tool receptacle 4. The sliding sleeve is mounted movably, preferably displaceably, in the outer sleeve 11, in which case it is designed in particular to be displaceable with respect to the first connection 6. Therefore the sliding sleeve can compensate for relative movements between the driving device 5 and the tool receptacle 4, thereby permitting a reliable transmission of measurement signals.

The second connection 7 is especially preferably designed to be elastic or resilient and comprises, for example, a spring element 42, in particular a spiral spring which prestresses the sliding sleeve against the tool receptacle 4. The spiral spring is accommodated with one end in the sliding sleeve and with the other end in the outer sleeve 11. The electrical measurement signal is conducted from the tool receptacle 4 to the driving device 5 and/or the shaft part 13A by way of the rounded hemispherical end 11A of the sliding sleeve, the spring element 42 and the outer sleeve 11.

As also shown in FIG. 2, the two connections 6, 7 come in contact with the tool receptacle 4 in different locations 9A, 9B which are separated from one another in space. At least a portion of the first connection 6, namely gearwheel 38, and the second connection 7 are arranged concentrically with the longitudinal axis of the driveshaft 13, wherein the gearwheel 38 radially surrounds the second connection 7.

Figure 3:
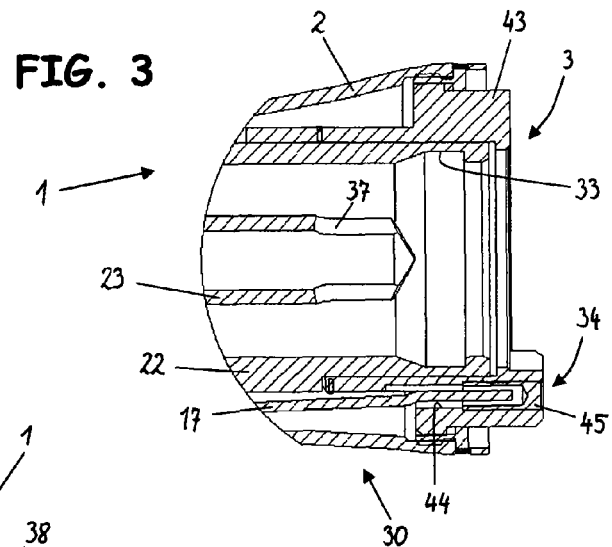
FIG. 3 is an enlarged view of the connecting device of the handpiece according to FIG. 1.

FIG. 3 shows the handle-part-side end of the handpiece 1 from FIG. 1 with the connecting device 3 on an enlarged scale. The connecting device 3 comprises a cylinder bushing 43 which is connected by connecting means, e.g., a thread to the outer sleeve 2. One end of the bearing sleeve 22 is inserted into the cylindrical inside bore of the cylinder bushing 43 so that the bearing sleeve 22 is supported by the cylinder bushing 43 in the handpiece 1.

In the outer wall of the cylinder bushing 43, in particular in a section having a thickened diameter, a receptacle is provided, in particular a longitudinal bore 44 which is part of the contact device 34. The contact device 34, designed as a plug contact, serves to connect the device 16 for transmission of electrical measurement signals, in particular one end of the wire 17, to a connecting part connectable to the connecting device 3. The end of the wire 17 protrudes into the longitudinal bore 44 and is surrounded by a socket 45 inserted into the longitudinal bore 44.

Figure 4:
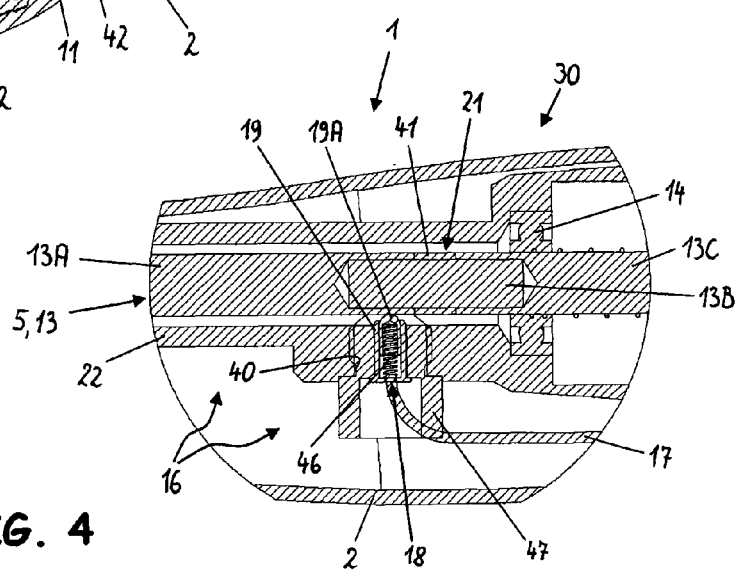
FIG. 4 is an enlarged view of the handle section of the handpiece according to FIG. 1.

FIG. 4 shows an enlarged detail of the handpiece 1 from FIG. 1 with the third connection 18 designed as a sliding contact for connecting the wire 17 to the driving device 5. The third connection 18 can be similar in design to the second connection 7 and comprise an outer sleeve 19 and a sliding sleeve with a rounded hemispherical end 19A. The sliding sleeve is accommodated movably, preferably displaceably, in an opening of the outer sleeve 19, which faces the driving device 5. The hemispherical end 19A is also facing the driving device 5 and contacts it. Through its mobility, the sliding sleeve can compensate for relative movements, in particular vibrations, between the driving device 5 and the wire 17, thereby allowing a reliable measurement signal transmission.

The third connection 18 is especially preferably designed to be elastic or resilient and comprise, for example, a spring element 46, in particular a spiral spring which prestresses the sliding sleeve against the driving device 5. The spiral spring is accommodated with one end in the sliding sleeve and with the other end in the outer sleeve 19.

For fastening the third connection 18 in the handpiece 1, the outer sleeve 19 is connected to a threaded bushing 47, e.g., by pressing or soldering. The threaded bushing 47 has on its outside a thread by which it is screwed into a borehole 40 of the bearing sleeve 22. The third connection 18 thus protrudes through the bearing sleeve 22 to the driving device 5.

The wire 17 passes through an additional opening in the outer sleeve 19 into the interior space of the outer sleeve 19, where it is connected to the spring element 46, the outer sleeve 19 and/or the sliding sleeve. The electrical measurement signal is conducted from the driveshaft part 13A to the wire 17 via the rounded hemispherical end 19A of the sliding sleeve and the spring element 46.

The insulation 21 with the shaft part 13B and the bushing 41 are arranged adjacent to the third connection 18.

The outer sleeve 2 of the handpiece 1 is made of electrically non-insulating material, preferably metallic. For electrical insulation of the assembly 16 for transmission of electrical measurement signals from the outer sleeve 2, an insulator or insulating portion is provided. At least the following parts can be configured as insulators or with insulating portions: the cartridge 49 with the bushing 27 and the retaining ring 28, the bearing element 48 of the ball bearing 15, the shaft part 13B, the bushing 41, the cylinder bushing 43 of the connecting device 3 and the threaded bushing 47 of the third connection 18. These components are manufactured from or coated with plastic and/or ceramic, for example. It is of course also possible to design other components of the handpiece 1 as electrical insulation means in addition or as an alternative to the components already mentioned, e.g., the bearing 14, 15 or the bearing sleeve 22.

The described embodiments are not limiting but instead include all embodiments which use or comprise the same basic function principle. Thus, the handpiece shown in FIG. 1 and the device for transmitting electrical measurement signals are designed for connecting electrically conducting tools without insulating sleeves. With such tools, the measurement signal is conducted from the tool which serves as an electrode to the drive unit via the tool receptacle.

In the case of tools such as files with sleeves made of plastic or with a plastic shaft, conduction of the electrical signal between the tool and the tool receptacle is interrupted by the plastic part. Thus, in order to use such tools, a contact device is necessary for connecting an electrically conducting section or part of the tool to the tool receptacle. Accordingly, all the handpieces described and presented in this document and all the embodiments thereof described and presented here are designed with or may be connected to a contact device or parts thereof so that the handpiece may also be used with insulated tools.

Possible embodiments of such a contact device are known from the '547 application. However, other contact devices may of course also be used with the inventive handpiece. The contact device comprises a U-shaped elastic wire with two legs arranged outside of the handpiece. In their front-end area, the two legs are curved inward. This curved area is situated essentially beneath the opening in the tool receptacle so that a tool chucked in the tool receptacle passes between the two legs and is contacted by the legs on two sides.

The basis of the U-shaped wire is connected to a sleeve and a conducting wire or cable accommodated therein, preferably by means of a clamp connection. The sleeve and the conducting wire are connected to the handpiece and accommodated at least partially therein. On one end the sleeve has a flange which is attached to the outer sleeve, preferably by adhesive bonding. The shaft of the sleeve protrudes outward through a bore in the outer sleeve, the diameter of the bore being smaller than the diameter of the flange.

On the end opposite the flange, the sleeve has a groove with two strips, wherein the diameter of the groove is somewhat smaller than the diameter of the base of the U-shaped wire. Since the side walls of the groove are designed to be elastic, they yield when the user presses the base against the strips and exerts some pressure toward the sides, so that the base enters the section of the groove connected to the strips and is secured by the strips which then spring back into their original position. To release the base, the user pulls the U-shaped wire so that the strips again yield to the side and release the base.

The conducting wire has a first end and a second end. The first wire end which is in contact with the base of the U-shaped wire clamped in the groove is accommodated in the sleeve-shaped shaft of the sleeve. The second end of the conducting wire is connected directly or indirectly by additional components of the handpiece to the tool receptacle. Further signal conduction from the tool receptacle takes place as described above.

In view of the many possible embodiments to which the disclosed principles may be applied, it should be recognized that the illustrated embodiments are only preferred examples and should not be taken as limiting in scope. Rather, the scope of protection is defined by the following claims. We therefore claim all that comes within the scope and spirit of these claims.

What is claimed is:

1. A dental handpiece for root canal treatment, comprising:
   an outer sleeve;
   a connecting device for connecting the handpiece to a control and analyzing unit, to a measurement circuit with a power source and to a drive unit;
   an electrically conductive tool receptacle; and
   a driving device drivable by the drive unit and comprising a driveshaft, wherein the driving device is configured to conduct an electrical signal and wherein the driving device is drivingly coupled to the tool receptacle at a first connection, and
   wherein the tool receptacle and the driving device are electrically connected at a second connection comprising a sliding contact for transmitting signals between the drive unit and the tool receptacle, wherein the second connection is mounted on the driveshaft and is prestressed into contact against the tool receptacle.

2. The dental handpiece according to claim 1, wherein the second connection is movable with respect to the first connection.

3. The dental handpiece according to claim 1, wherein the second connection comprises a resilient component.

4. The dental handpiece according to claim 1, wherein the second connection is at least partially arranged in a receptacle of the driveshaft.

5. The dental handpiece according to claim 1, wherein the first and second connections are positioned to contact the tool receptacle at different locations.

6. The dental handpiece according to claim 1, wherein the second connection has a pin or a sleeve with a rounded end.

7. The dental handpiece according to claim 1, wherein the handpiece has a handle part, a neck part arranged at an angle to the handle part and a handpiece head arranged at an angle to the neck part, wherein the tool receptacle is arranged in the handpiece head, and the driving device comprises an essentially straight driveshaft, which passes through the handle part and the neck part.

8. The dental handpiece according to claim 7, wherein the driveshaft comprises multiple shaft parts which are connected together in a twist-proof manner.

9. The dental handpiece according to claim 7, wherein the driveshaft is supported by only two bearings, in particular by two roller bearings.

10. The dental handpiece according to claim 1, wherein at least a portion of at least one of the tool receptacle, the driving device, the connecting device and the second connection is provided with a conductive coating, an electrical conductivity of the coating being higher than the electrical conductivity of steel.

11. The dental handpiece according to claim 10, wherein the coating is constructed in multiple layers, wherein at least one of the layers is designed as an adhesive.

12. The dental handpiece according to claim 1, comprising an electrically conducting wire which is electrically connected to the driving device for conducting the electrical signals away from the driving device.

13. The dental handpiece according to claim 12, comprising
a third connection for connecting the wire to the driving device.

14. The dental handpiece according to claim 13, wherein the third connection comprises a resilient component.

15. The dental handpiece according to claim 13, wherein the third connection at least partially occupies a bearing sleeve of the drive unit.

16. A dental handpiece for root canal treatment, comprising:
an outer sleeve;
a connecting device for electrically connecting the handpiece to a control and analyzing unit, to a measurement circuit with a power source and to a drive unit;
a tool receptacle, a driving device comprising a drive shaft for transmitting a driving motion from the drive unit to the tool receptacle;
an assembly for transmitting electrical measurement signals through the handpiece, the assembly comprising at least a part of the drive shaft and an electrical insulator arranged on the drive shaft which is configured to electrically insulate the drive shaft from an electrically conductive component that is releasably connectable to the connecting device, wherein the electrical insulator is configured as part of the drive shaft.

17. The dental handpiece according to claim 16, wherein the drive shaft comprises multiple shaft parts, and the electrical insulator comprises at least one shaft part.

18. The dental handpiece according to claim 16, wherein the drive shaft comprises multiple shaft parts, and the electrical insulator comprises at least one bushing arranged between two shaft parts.

19. The dental handpiece according to claim 16, wherein the insulator is a first insulator, further comprising
an outer sleeve of an electrically non-insulating material and a second insulator for electrically insulating the outer sleeve from the assembly for transmission of electrical measurement signals.

20. The dental handpiece according to claim 16, wherein the assembly for transmitting electrical measurement signals further comprises at least one electrically conducting wire having a first and a second end, wherein the first end is electrically connected to the driveshaft and the second end is electrically connected to a contact device at the connecting device, and wherein the electric insulator which is configured as part of the drive shaft is arranged such that it electrically isolates the wire from the electrically conductive component that is releasably connectable to the connecting device.

\* \* \* \* \*